United States Patent
Jeon et al.

(10) Patent No.: US 9,265,707 B2
(45) Date of Patent: Feb. 23, 2016

(54) COSMETIC COMPOSITION COMPRISING COUMESTROL OR A BEAN EXTRACT CONTAINING COUMESTROL FOR SKIN CARE

(75) Inventors: Hee Young Jeon, Gyeonggi-do (KR); Jeong Kee Kim, Gyeonggi-do (KR); Su Kyung Kim, Gyeonggi-do (KR); Dae Bang Seo, Gyeonggi-do (KR); Sang Jun Lee, Gyeonggi-do (KR)

(73) Assignee: AMOREPACIFIC CORPORATION, Seoul (KR)

( * ) Notice: Subject to any disclaimer, the term of this patent is extended or adjusted under 35 U.S.C. 154(b) by 0 days.

(21) Appl. No.: 13/637,959

(22) PCT Filed: Mar. 31, 2011

(86) PCT No.: PCT/KR2011/002218
§ 371 (c)(1),
(2), (4) Date: Dec. 7, 2012

(87) PCT Pub. No.: WO2011/122869
PCT Pub. Date: Oct. 6, 2011

(65) Prior Publication Data
US 2013/0071342 A1    Mar. 21, 2013

(30) Foreign Application Priority Data
Mar. 31, 2010   (KR) ................. 10-2010-0029164

(51) Int. Cl.
*A61K 8/97* (2006.01)
*A61Q 19/00* (2006.01)
*A61Q 19/08* (2006.01)
*A61K 8/49* (2006.01)

(52) U.S. Cl.
CPC . *A61K 8/498* (2013.01); *A61K 8/97* (2013.01); *A61Q 19/00* (2013.01); *A61Q 19/08* (2013.01)

(58) Field of Classification Search
None
See application file for complete search history.

(56) References Cited

U.S. PATENT DOCUMENTS

2005/0137176 A1    6/2005  Ferraris et al.
2005/0267047 A1*   12/2005 Jia et al. .......................... 514/23
2008/0107776 A1    5/2008  Prakash et al.

FOREIGN PATENT DOCUMENTS

| JP | 6-321763 A | 11/1994 |
|---|---|---|
| JP | 2002-516983 A | 6/2002 |
| KR | 10-2002-0000980 A | 1/2002 |
| KR | 10-0628518 B1 | 9/2006 |

\* cited by examiner

*Primary Examiner* — David J Blanchard
*Assistant Examiner* — Sarah Chickos
(74) *Attorney, Agent, or Firm* — Dickstein Shapiro LLP

(57) ABSTRACT

The present invention relates to a cosmetic composition for skin care, comprising coumestrol or a bean extract containing coumestrol.

15 Claims, No Drawings

COSMETIC COMPOSITION COMPRISING COUMESTROL OR A BEAN EXTRACT CONTAINING COUMESTROL FOR SKIN CARE

TECHNICAL FIELD

The present disclosure relates to a skin care composition comprising coumestrol or a bean extract comprising coumestrol.

BACKGROUND ART

As the average life span of human beings increases, it is becoming important how to maintain youth for a long time rather than how long to live. Aging is a process that cannot be avoided as one gets old. In particular, in the modern society where environmental pollution and stress are becoming severer and exposure to UV is increasing, aging starts earlier than before.

All human organs age gradually and skin aging is greatly affected by the external environment. Most of early skin aging begins with skin dryness. As the skin becomes dry, it loses elasticity and becomes prone to wrinkling. As skin aging proceeds, it takes longer for skin regeneration, the skin becomes rough due to keratinization, wrinkles are formed because of decreased collagen synthesis, pigmentation such as freckles, live spot, etc. occurs due to decreased defense against UV, and the skin becomes vulnerable to drugs or external stimulation because of decreased skin protection.

DISCLOSURE

Technical Problem

The present disclosure is directed to providing a skin care composition comprising coumestrol or a bean extract comprising coumestrol as an active ingredient.

The present disclosure is also directed to providing a skin care composition as a cosmetic composition comprising coumestrol or a bean extract comprising coumestrol as an active ingredient.

Technical Solution

In an aspect, the present disclosure provides a skin care composition comprising coumestrol or a bean extract comprising coumestrol as an active ingredient.

Advantageous Effects

The skin care composition according to the present disclosure provides the effect of improving skin elasticity, improving skin wrinkles, whitening skin, moisturizing skin, anti-inflammation, anti-bacteria, preventing skin aging, anti-oxidation, improving acne, improving atopic dermatitis, relieving skin irritation, maintaining skin homeostasis and relieving or improving skin allergy, and is useful in wide applications including, for example, cosmetics or foods.

MODE FOR INVENTION

As used herein, "extract" means a substance extracted from a natural substance, regardless of extraction method or ingredients. The term is used in a broad sense including, for example, ingredients soluble in water or an organic solvent extracted from a natural substance using the solvent, or specific ingredients of a natural substance such as oil extracted therefrom.

As used herein, "skin" means the tissue covering the body surface of an animal and is used in the broadest sense, including not only the tissue that covers the face or body but also the scalp and hair.

As used herein, "skin care" includes any treatment or care to improve the appearance and health of skin.

Hereinafter, the present disclosure is described in further detail.

In an aspect, the present disclosure provides a skin care composition comprising coumestrol or a bean extract comprising coumestrol as an active ingredient.

Coumestrol (CMS; 3,9-dihydroxy-6H-benzofuro(3,2-c)(1)benzopyran-6-one) has a structure of Chemical Formula I:

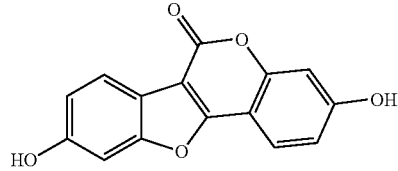

Chemical Formula 1

Coumestrol is one of phytoestrogens and is usually found in the seed, root or leaf of plants in the family Leguminosae or Compositae. It can be classified as a coumestan-like isoflavonoid and is known to have an estrogenic effect.

In an exemplary embodiment of the present disclosure, the skin care composition comprises coumestrol, a natural substance comprising coumestrol or an extract thereof. In another exemplary embodiment of the present disclosure, the natural substance comprising coumestrol may be one or more bean selected from soybean, pea, mung bean and sprouted beans sprouted therefrom, red clover (alfalfa), Brussels sprout, or the like. In another exemplary embodiment of the present disclosure, the natural substance comprising coumestrol may be bean.

In an exemplary embodiment of the present disclosure, the bean may be any plant comprising coumestrol in the family Leguminosae, without particular limitation. For example, the bean that can be used in the present disclosure may be one for bean paste, bean curd, namul, rice cooking or green bean. The bean varieties for bean paste or bean curd include daepung, hojang, jangwon, daehwang, sodam, songhak, daewon, jinpum, danbaek, duyu, shinpaldal, taegwang, manli, jangsu, muhan, baegun, saeal, hwangkeum and jangyeop. The bean varieties for namul include shinhwa, sowon, anpyeong, seonam, dachae, sorok, soho, somyeong, dawon, pungsan-namul, iksan-namul, sobaek-namul, gwangan, danyeop and eunha. The bean varieties for rice cooking include cheongja, heukcheong, galmi, seonheuk, geomjeong-kong and ilpum-geomjeong-kong. And, the bean varieties for green bean include daol, shinrok, saeul, geomjeongeul, seokryang-putkong, hwaeom-putkong and keuneul. In another exemplary embodiment of the present disclosure, the bean may be one that can be sprouted and is resistant to damage from disease and harmful insects. Such bean varieties include, for example, shinhwa, sowon, anpyeong, seonam, dachae, sorok, soho, somyeong, dawon, pungsan-namul, iksan-namul, sobaek-namul, gwangan, danyeop and eunha.

In an exemplary embodiment of the present disclosure, the natural substance or the extract thereof may comprise a large quantity of coumestrol. Specifically, it may comprise 0.01-50 wt %, more specifically 0.1-30 wt % of coumestrol based on the total weight of the natural substance or the extract thereof.

In an exemplary embodiment of the present disclosure, the extract of the natural substance comprising coumestrol may be obtained by extracting the natural substance comprising coumestrol with water or ethanol at normal or elevated temperature, completely concentrating the resulting extract and dispersing again in water, and fractionating with one or more solvent of equal volume selected from hexane, dichloromethane, chloroform, ethyl acetate, butanol, ethanol, methanol and water. However, the extraction method is not limited thereto and any extraction method may be employed.

In an exemplary embodiment of the present disclosure, the skin care composition may be a skin care composition for improving skin elasticity or wrinkles. The coumestrol included in the composition as the active ingredient inhibits the expression of matrix metalloproteinase-1 (MMP-1) which may act as collagenase, promotes the synthesis of type I pN collagen, suppresses glycation of skin cells, and promotes the production of ATP in cells. The composition comprising coumestrol as an active ingredient may provide the superior effect of improving skin elasticity and wrinkles through these actions. Particularly, the composition provides an excellent effect of improving skin wrinkles induced by UV.

In an exemplary embodiment of the present disclosure, the skin care composition may be a composition for whitening skin. The coumestrol included in the composition as the active ingredient significantly scavenges reactive oxygen species produced by skin aging or UV irradiation, inhibits melanin production, and reduces glycation of skin cells. The composition comprising coumestrol as an active ingredient may provide an excellent skin whitening effect through these actions.

In an exemplary embodiment of the present disclosure, the skin care composition may be a composition for moisturizing skin. The coumestrol included in the composition as the active ingredient reduces loss of moisture from the skin, and has an excellent ability of regenerating the skin by promoting ATP production in cells. The composition comprising coumestrol as an active ingredient may provide an excellent skin moisturizing effect through these actions.

In an exemplary embodiment of the present disclosure, the skin care composition may be an anti-inflammatory or antibacterial composition. The coumestrol included in the composition as the active ingredient inhibits the production of prostaglandin E2 (PGE2), promotes ATP production in cells, suppresses inflammatory response through inhibition of cyclooxygenase-2 (COX-2) biosynthesis induced by lipopolysaccharides (LPS), and protects the skin from microbes or bacteria. The composition comprising coumestrol as an active ingredient may provide excellent anti-inflammatory and antibacterial effects through these actions.

In an exemplary embodiment of the present disclosure, the skin care composition may be a composition for preventing skin aging or a composition for anti-oxidation. With aging, the content or arrangement of collagen, elastin, hyaluronic acid and glycoproteins changes or decreases. Also, the skin receives oxidative stress from free radicals or reactive oxygen species. The coumestrol included in the composition as the active ingredient has an excellent effect of scavenging reactive oxygen species, improves skin elasticity and skin wrinkles, has superior skin whitening and skin moisturizing effects, and provides excellent effect of inhibiting skin aging or oxidation through promotion of energy metabolism in skin cells. The composition comprising coumestrol as an active ingredient may provide excellent effect of preventing skin aging or oxidation through these actions.

In an exemplary embodiment of the present disclosure, the skin care composition may be a composition for improving acne. The coumestrol included in the composition as the active ingredient inhibits the production of PGE2, controls sebum and suppresses inflammatory response through inhibition of COX-2 biosynthesis induced by LPS, and thus provides the effect of improving acne and skin trouble. The composition comprising coumestrol as an active ingredient may provide the effect of improving acne through these actions.

In an exemplary embodiment of the present disclosure, the skin care composition may be a composition for improving atopic dermatitis. Since the coumestrol included in the composition as the active ingredient has excellent skin moisturizing, anti-inflammatory and antibacterial effects as well as excellent ability of regenerating skin cells, it can improve atopic dermatitis.

In an exemplary embodiment of the present disclosure, the skin care composition may be a composition for relieving skin irritation or maintaining skin homeostasis. The coumestrol included in the composition as the active ingredient inhibits the production of PGE2, suppresses inflammatory response through inhibition of COX-2 biosynthesis induced by LPS, and thus provides the effect of preventing skin inflammation and damage caused by harmful external substances. The composition comprising coumestrol as an active ingredient may provide the effect of protecting the skin by relieving skin irritation caused by various harmful external factors such as chemicals, air pollutants, UV, etc. and maintaining skin homeostasis through these actions.

In an exemplary embodiment of the present disclosure, the skin care composition may be a composition for relieving or preventing skin allergy. The coumestrol included in the composition as the active ingredient has superior skin moisturizing, anti-inflammatory and antibacterial effects as well as excellent ability of regenerating skin cells. Accordingly, the composition comprising coumestrol as an active ingredient may have an effect of relieving or preventing skin allergy.

The composition according to an embodiment of the present disclosure may comprise 0.001-30 wt %, specifically 0.01-10 wt %, more specifically 0.1-5 wt %, of coumestrol or a bean extract comprising coumestrol based on the total weight of the composition. When the coumestrol or the bean extract comprising coumestrol is included in the above-described range, the intended effect of the present disclosure can be adequately achieved while both stability and safety are satisfied and favorable cost-effectiveness may be achieved.

The skin care composition according to an embodiment of the present disclosure may be a cosmetic composition. The cosmetic composition may comprise a cosmetologically or dermatologically allowable medium or base. It may be provided in any topically applicable form including, for example, solution, gel, powder, paste, anhydrous slurry, oil-in-water emulsion, water-in-oil emulsion, multiemulsion, suspension, microemulsion, microcapsule, microgranule, ionic (liposome) or non-ionic vesicular dispersion, foam, or an aerosol composition comprising a pressurized propellant. Such compositions may be prepared by a method commonly employed in the art.

The cosmetic composition may further comprise fatty substance, organic solvent, solubilizer, thickening agent, gelling agent, softening agent, antioxidant, suspending agent, stabilizer, foaming agent, aromatic, surfactant, water, ionic or non-ionic emulsifier, filler, sequestrant, chelating agent, preservative, vitamin, blocker, hydrating agent, essential oil, dye, pigment, hydrophilic or lipophilic active agent, lipid vesicle or other adjuvant commonly used in the field of cosmetics or dermatology. The adjuvant is added in an amount commonly used in the field of cosmetics or dermatology.

The cosmetic composition is not particularly limited with regard to the formulation thereof and the formulation may be determined appropriately depending on purposes. For example, the cosmetic composition may be provided as one or more formulation selected from a group consisting of toilet water, lotion, essence, cream, ointment, gel, pack, patch, spray, powder foundation, emulsion foundation, conceal stick, hand or foot lotion, hand or foot cream, hand or foot oil, hand or foot essence, hand or foot cleanser, soap, cleansing cream, cleansing lotion, cleansing foam and cleansing water, but is not limited thereto.

The skin care composition according to an embodiment of the present disclosure may be a food composition. The food composition may be formulated into, for example, tablet, granule, drink, caramel, etc., but is not particularly limited thereto. Each formulation of the food composition may comprise, in addition to the active ingredient, ingredients which are commonly used in the art. The ingredients may be selected by those skilled in the art without difficulty considering the purpose of use and may provide a synergic effect.

Determination of the dose of the active ingredient is within the level of those skilled in the art. For example, the dose may be 0.1-5000 mg/kg/day, more specifically 50-500 mg/kg/day, but is not limited thereto, and may be varied with various factors including the age, physical condition, complication, etc. of a subject to be treated.

The features and effects of the present disclosure will be described in detail through test examples. However, the following test examples are provided for illustrative purposes only and are not intended to limit the scope of the present disclosure.

Test Example 1

Evaluation of Effect of Scavenging UVB-Induced Reactive Oxygen Species (ROS)

2',7'-Dichlorodihydrofluorescein diacetate (DCFH-DA; Molecular Probes, Inc., OR, USA) was used to evaluate the coumestrol's effect of scavenging UVB-induced ROS. DCFH-DA is an fat-soluble substance well known as a detector of ROS in cells. It is easily absorbed by cells and turned into water-soluble 2',7'-dichlorodihydrofluorescein as a result of hydrolysis of the acetate group by esterase in the cells. Since it is turned to 2',7'-dichlorofluorescein (DCF) which emits fluorescence after reaction with intracellular oxidizing agents, the quantity of intracellular ROS can be evaluated by measuring the intensity of fluorescence from cells treated with DCFH-DA.

Keratinocytes (acquired from Dr. Fusenig at German Cancer Research Center) were seeded onto a 96-well black plate (Greiner BioOne Inc., NC, USA) for fluorescence measurement at a density of $1 \times 10^4$ cells per well and cultured for 24 hours. Then, the cells were treated with coumestrol diluted in fresh FBS-free medium to a final concentration of 0.01, 0.1 or 1 μM. After addition of the test substance, the cells were cultured for 24 hours. After removing the remaining medium by washing with HEPES-buffered control salt solution (HCSS), 20 μM DCFH-DA in 100 μL of HCSS was added. After culturing for 20 minutes at 37° C. and 5% $CO_2$, the cells were washed with HCSS. Then, after adding 100 μL of HCSS, the cells were irradiated with UVB of 30 $mJ/cm^2$ to induce production of ROS. Subsequently, the cells were cultured for 3 hours at 37° C. and 5% $CO_2$ with coumestrol diluted in HCSS to the same concentration. The fluorescence intensity of DCF was measured with the Wallac VICTOR2 fluorometer (Wallac, Turku, Finland) at excitation wavelength of 485 nm and emission wavelength of 530 nm. ROS scavenging effect (%) relative to the control group was calculated from the measured fluorescence intensity. The result is given in Table 1.

TABLE 1

|  | ROS scavenging effect (%) |
| --- | --- |
| UV-treated control | 0 |
| Coumestrol, 0.01 μM | 18.7 |
| Coumestrol, 0.1 μM | 25.6 |
| Coumestrol, 1 μM | 55.1 |

As seen from Table 1, coumestrol has the ability of scavenging UVB-induced ROS, and the effect increases with the concentration of coumestrol. Accordingly, a composition comprising coumestrol may provide the effect of inhibiting skin oxidation caused by UV, inhibiting photoaging, and whitening skin.

Test Example 2

Evaluation of Effect of Inhibiting UV-Induced MMP-1 Expression

Human fibroblasts (CAS-C-004-5C, Invitrogen, CA, USA) were used to evaluate the coumestrol's effect of inhibiting UV-induced MMP-1 expression. The cells were seeded onto a 24-well plate at a density of $1 \times 10^4$ cells per well and cultured for about 24 hours in a medium containing 10% FBS until ~about 80% confluency. After replacing the medium with an FBS-free medium, the cells were cultured for 24 hours. After washing once with PBS and adding 100 μL of PBS, the cells were irradiated with UVB of 15 $mJ/cm^2$. After removing the PBS, the cells were treated with coumestrol diluted to a final concentration of 0.01, 0.1 or 1 μM in a fresh FBS-free medium. Expression of MMP-1 was evaluated 48 hours after the treatment with the test substance. The expression of MMP-1 was evaluated using an enzyme-linked immunosorbent assay (ELISA) kit (RPN 2610; Biotrak Amersham Pharmacia Biotech, UK) after collecting a supernatant from the cell culture. The quantity of MMP-1 was determined from the total protein quantity. MMP1 activity (%) was calculated and the result given in Table 2.

TABLE 2

|  | MMP1 activity (%) |
| --- | --- |
| Untreated control | 100 |
| UV-treated control | 132 |
| Coumestrol, 0.01 μM | 115 |
| Coumestrol, 0.1 μM | 102 |
| Coumestrol, 1 μM | 98 |

As seen from Table 2, coumestrol has the ability of inhibiting UV-induced MMP-1 activity, and the effect increases with the concentration of coumestrol. Accordingly, a composition comprising coumestrol may improve skin elasticity and wrinkles by inhibiting the breakdown of collagen.

Test Example 3

Evaluation of Effect on Type I pN Collagen Synthesis

Human fibroblasts (CAS-C-004-5C, Invitrogen, CA, USA) were used to evaluate the coumestrol's effect on type I pN collagen synthesis. The cells were seeded onto a 24-well plate at a density of $1 \times 10^4$ cells per well and cultured for about 24 hours in a medium containing 10% FBS until ~about 80% confluency. The cells were treated with coumestrol diluted to a final concentration of 0.01, 0.1 or 1 µM in a fresh FBS-free medium. The synthesized quantity of type I pN collagen was measured using a procollagen type I C-peptide (PIP) EIA kit (MK101; Takara Shuzo, Kyoto, Japan) by collecting a supernatant from the cell culture 48 hours after the treatment with the test substance. The quantity of type I pN collagen was determined from the total protein quantity. The synthesized quantity of type I pN collagen (%) was calculated and the result given in Table 3.

TABLE 3

|  | Synthesis of type I pN collagen (%) |
|---|---|
| Untreated control | 100 |
| Coumestrol, 0.01 µM | 115 |
| Coumestrol, 0.1 µM | 126 |
| Coumestrol, 1 µM | 129 |

As seen from Table 3, coumestrol promotes the synthesis of type I pN collagen. Accordingly, a composition comprising coumestrol may improve skin elasticity and wrinkles.

Test Example 4

Evaluation of Effect of Inhibiting Glycation of Skin Cells

Human fibroblasts (CAS-C-004-5C, Invitrogen, CA, USA) were used to evaluate the coumestrol's effect of inhibiting glycation of skin cells. The cells were seeded onto a 6-well plate at a density of $5 \times 10^4$ cells per well and cultured for about 24 hours in a medium containing 10% FBS until ~about 80% confluency. After washing once with PBS and adding 100 µL of PBS, the cells were irradiated with UVB of 50 mJ/cm². After removing the PBS, the cells were treated with coumestrol diluted to a final concentration of 2.5 µM in a fresh FBS-free medium. Glycation of skin cells was evaluated using the Oxiselect™ advanced glycation end product (AGE) ELISA kit 24 hours after the treatment with the test substance. The concentration of the glycation end product was measured and is shown in Table 4.

TABLE 4

|  | Concentration of glycation end product (µg/mL) |
|---|---|
| Untreated control | 0.156 |
| Coumestrol, 2.5 µM | 0.077 |

As seen from Table 4, coumestrol inhibits glycation of the skin cells. Accordingly, a composition comprising coumestrol may improve skin elasticity and provide a skin whitening effect.

Test Example 5

Evaluation of Effect on ATP Production

Following treatment of human fibroblasts (CAS-C-004-5C, Invitrogen, CA, USA) as in Test Example 4, ATP production in the cells was evaluated using an ATP determination kit (Invitrogen, A22066). The measured ATP concentration is shown in Table 5.

TABLE 5

|  | Concentration of ATP (nM) |
|---|---|
| Untreated control | 803 |
| Coumestrol, 2.5 µM | 917 |

As seen from Table 5, coumestrol promotes the production of ATP in cells. Accordingly, a composition comprising coumestrol may promote skin regeneration and improve skin elasticity by promoting energy metabolism of the skin cells and activating the skin cells.

Test Example 6

Evaluation of Effect of Inhibiting Melanin Production

Mouse melanocytes (MeI-Ab cells) derived from C57BL/6 mouse were cultured in Dulbecco's modified Eagles medium (DMEM) containing 10% FBS, 100 nM 2-O-tetradecanoylphorbol-13-acetate and 1 nM cholera toxin at 37° C. and 5% $CO_2$. The cultured MeI-Ab cells were detached with 0.25% trypsin-EDTA and cultured on a 24-well plate, with $10^5$ cells/well. From day 2, 0.01, 0.1 or 1 µM coumestrol was added for 3 consecutive days. Subsequently, after removing the medium and washing with PBS, the cells were suspended in 1 N sodium hydroxide and absorbance was measured at 400 nm. 10 µM hydroquinone, which is known to have an excellent effect of inhibiting melanin production, was used as positive control. The melanin production inhibiting effect (%) was calculated from the measured absorbance and is given in Table 6.

TABLE 6

|  | Melanin production inhibiting effect (%) |
|---|---|
| Coumestrol, 0.01 µM | 1.2 |
| Coumestrol, 0.1 µM | 24.4 |
| Coumestrol, 1 µM | 30.1 |
| Hydroquinone, 10 µM (positive control) | 41.1 |

As seen from Table 6, coumestrol has an excellent effect of inhibiting melanin production. Accordingly, a composition comprising coumestrol may have a superior skin whitening effect.

Test Example 7

Evaluation of Effect of Inhibiting Prostaglandin E2 (PGE2) Production

The coumestrol's effect of inhibiting prostaglandin E2 production was tested as follows. Human fibroblasts (CAS-C-004-5C, Invitrogen, CA, USA) were cultured for 24 hours in a $CO_2$ incubator. After replacing the medium with a fresh FBS-free medium and culturing for 2 hours, the cells were treated with coumestrol diluted to a final concentration of 0.01, 0.1 or 1 µM in a fresh FBS-free medium. The cells were then cultured for 2 hours at 37° C. in a 5% (v/v) $CO_2$ incubator. Subsequently, after treating with 50 µM Calcium Ionophore A23187 and arachidonic acid for 5 minutes to stimulate prostaglandin E2, the cells were lysed and prostaglandin E2 was quantitated by measuring absorbance at 450 nm using an ELISA reader. The result is shown in Table 7. The inhibiting effect (%) was calculated relative to the coumestrol-untreated group. Measurement was made 5 times and the result was averaged.

TABLE 7

| | Prostaglandin E2 production inhibiting effect (%) |
|---|---|
| Coumestrol, 0.01 µM | 12.8 |
| Coumestrol, 0.1 µM | 24.8 |
| Coumestrol, 1 µM | 38.2 |

As seen from Table 7, coumestrol inhibits the production of prostaglandin E2. Accordingly, a composition comprising coumestrol has an anti-inflammatory effect and may prevent sebum secretion, relieve skin trouble and improve acne and skin allergy.

Test Example 8

Evaluation of Effect of Inhibiting Cyclooxygenase-2 (COX-2) Biosynthesis Induced by Lipopolysaccharides (LPS)

Human fibroblasts (CAS-C-004-5C, Invitrogen, CA, USA) were used to evaluate the coumestrol's effect of inhibiting COX-2 biosynthesis. The cells were seeded onto a 6-well plate at a density of $5 \times 10^4$ cells per well and cultured for about 24 hours in a medium containing 10% FBS until ~80% confluency. The cells were treated with coumestrol diluted to a final concentration of 0.01, 0.1 or 1 µM in a fresh FBS-free medium and then cultured for 24 hours at 37° C. in a 5% (v/v) $CO_2$ incubator. The cells were harvested and the produced COX-2 was quantitated by western blotting. COX-2 expression level (%) relative to the control group was calculated and is given in Table 8.

TABLE 8

| | COX-2 expression level (% relative to control) |
|---|---|
| Coumestrol, 0.01 µM | 89 |
| Coumestrol, 0.1 µM | 81 |
| Coumestrol, 1 µM | 64 |

As seen from Table 8, coumestrol inhibits the biosynthesis of COX-2 induced by LPS. Accordingly, a composition comprising coumestrol may provide an anti-inflammatory effect and improve acne and skin allergy.

Test Example 9

Evaluation of Effect of Improving Atopic Dermatitis

Thirty people between 10s and 50s who were diagnosed with atopic symptoms (itchiness, blisters or severe dryness) or showed atopy-like symptoms were divided into two groups and given an ointment containing 0.1% coumestrol or one without containing coumestrol (control), respectively. They were asked to apply the ointment for 12 weeks, twice a day, at the sites of atopic symptoms. 12 weeks later, the improvement of the atopic symptoms was examined using a questionnaire. Improvement of typical symptoms of atopic dermatitis including "itchiness", "dryness", "keratinization", "dandruff", "erythema", "swelling", "skin fissure" and "ooze and eczema" was examined. The subjects were asked to score the improvement of the symptoms and the result was averaged to evaluate the improvement of atopic dermatitis. The result is given in Table 9.

TABLE 9

| | Number of subjects | | | |
|---|---|---|---|---|
| | Remarkably improved | Improved | Not changed | Aggravated |
| Control | 1 | 4 | 8 | 2 |
| Coumestrol, 0.1% | 5 | 8 | 2 | 0 |

As seen from Table 9, coumestrol and a composition comprising coumestrol have an effect of improving atopic dermatitis.

Test Example 10

Evaluation of Effect of Improving Skin Moisturization

In order to evaluate the improvement of skin moisturizing ability, transepidermal water loss was measured for the subjects of Test Example 9 under constant-temperature, constant-humidity conditions (24° C., RH 40%) using a corneometer. The result was averaged and is given in Table 10.

TABLE 10

| | Transepidermal water loss (%) | | | |
|---|---|---|---|---|
| | 1 week later | 4 weeks later | 8 weeks later | 12 weeks later |
| Control | 34 | 39 | 41 | 36 |
| Coumestrol, 0.1% | 30 | 32 | 26 | 15 |

As seen from Table 10, coumestrol inhibits transepidermal water loss and the effect increases with time. Accordingly, a composition comprising coumestrol may provide a skin moisturizing effect.

Formulation examples of the composition according to the present disclosure are described hereinafter. However, the scope of the present disclosure is not limited to the following examples.

Formulation Example 1

Softening Lotion

A softening lotion is prepared according to a commonly employed method with the ingredients described in Table 11.

TABLE 11

| Ingredients | Content (wt %) |
|---|---|
| Coumestrol | 1.0 |
| Glycerin | 3.0 |
| Butylene glycol | 2.0 |
| Propylene glycol | 2.0 |
| Carboxyvinyl polymer | 0.1 |
| PEG-12 nonyl phenyl ether | 0.2 |
| Polysorbate 80 | 0.4 |
| Ethanol | 10.0 |
| Triethanolamine | 0.1 |
| Antiseptic, colorant and fragrance | adequate |
| Purified water | balance |

Formulation Example 2

Nourishing Lotion

A nourishing lotion is prepared according to a commonly employed method with the ingredients described in Table 12.

TABLE 12

| Ingredients | Content (wt %) |
| --- | --- |
| Coumestrol | 2.0 |
| Glycerin | 3.0 |
| Butylene glycol | 3.0 |
| Propylene glycol | 3.0 |
| Carboxyvinyl polymer | 0.1 |
| Beeswax | 4.0 |
| Polysorbate 60 | 1.5 |
| Capric/caprylic triglyceride | 5.0 |
| Squalane | 5.0 |
| Sorbitan sesquiolate | 1.5 |
| Liquid paraffin | 0.5 |
| Cetearyl alcohol | 1.0 |
| Triethanolamine | 0.2 |
| Antiseptic, colorant and fragrance | adequate |
| Purified water | balance |

Formulation Example 3

Nourishing Cream

A nourishing cream is prepared according to a commonly employed method with the ingredients described in Table 13.

TABLE 13

| Ingredients | Content (wt %) |
| --- | --- |
| Coumestrol | 3.0 |
| Glycerin | 3.0 |
| Butylene glycol | 3.0 |
| Liquid paraffin | 7.0 |
| β-Glucan | 7.0 |
| Carbomer | 0.1 |
| Capric/caprylic triglyceride | 3.0 |
| Squalane | 5.0 |
| Cetearyl glucoside | 1.5 |
| Sorbitan stearate | 0.4 |
| Polysorbate 60 | 1.2 |
| Triethanolamine | 0.1 |
| Antiseptic, colorant and fragrance | adequate |
| Purified water | balance |

Formulation Example 4

Tablet

Coumestrol (80 mg), vitamin E (9 mg), vitamin C (9 mg), galactooligosaccharide (200 mg), lactose (60 mg) and maltose (140 mg) are mixed and granulated using a fluidized bed dryer. After adding sugar ester (6 mg), the resulting composition (500 mg) is prepared into a tablet according to a commonly employed method.

Formulation Example 5

Drink

Coumestrol (80 mg), vitamin E (9 mg), vitamin C (9 mg), glucose (10 g), citric acid (0.6 g) and oligosaccharide syrup (25 g) are mixed. After adding purified water (300 mL), 200 mL of the resulting mixture is filled in a bottle. Then, a drink is prepared by sterilizing at 130° C. for 4-5 seconds.

Those skilled in the art will appreciate that the present disclosure may be changed and modified variously within the scope of the present disclosure.

The invention claimed is:

1. A method for inducing an anti-inflammatory or anti-bacterial effect in a subject in need thereof, comprising administering to the skin of the subject a pharmaceutical or cosmetic composition containing coumestrol or a bean extract comprising coumestrol in an amount effective to inducing an anti-inflammatory or anti-bacterial effect in the subject.

2. A method for improving atopic dermatitis in a subject in need thereof, comprising administering to the skin of the subject a pharmaceutical or cosmetic composition containing coumestrol or a bean extract comprising coumestrol in an amount effective to improve the subject's atopic dermatitis.

3. A method for improving a skin allergy in a subject in need thereof, comprising administering to the skin of the subject a pharmaceutical or cosmetic composition containing coumestrol or a bean extract comprising coumestrol in an amount effective to improve the subject's skin allergy.

4. The method of claim 1, wherein coumestrol is administered in a dose of about 0.1-5000 mg/kg/day.

5. The method of claim 4, wherein coumestrol is administered in a dose of about 50-500 mg/kg/day.

6. The method of claim 1, wherein the pharmaceutical or cosmetic composition comprises 0.001-30 wt % of coumestrol or the bean extract comprising coumestrol.

7. The method of claim 6, wherein the pharmaceutical or cosmetic composition comprises 0.1-5 wt % of coumestrol or the bean extract comprising coumestrol.

8. The method of claim 2, wherein coumestrol is administered in a dose of about 0.1-5000 mg/kg/day.

9. The method of claim 8, wherein coumestrol is administered in a dose of about 50-500 mg/kg/day.

10. The method of claim 2, wherein the pharmaceutical or cosmetic composition comprises 0.001-30 wt % of coumestrol or the bean extract comprising coumestrol.

11. The method of claim 10, wherein the pharmaceutical or cosmetic composition comprises 0.1-5 wt % of coumestrol or the bean extract comprising coumestrol.

12. The method of claim 3, wherein coumestrol is administered in a dose of about 0.1-5000 mg/kg/day.

13. The method of claim 12, wherein coumestrol is administered in a dose of about 50-500 mg/kg/day.

14. The method of claim 3, wherein the pharmaceutical or cosmetic composition comprises 0.001-30 wt % of coumestrol or the bean extract comprising coumestrol.

15. The method of claim 14, wherein the pharmaceutical or cosmetic composition comprises 0.1-5 wt % of coumestrol or the bean extract comprising coumestrol.

* * * * *